US00PP10812P

United States Patent [19]

Glicenstein

[11] Patent Number: Plant 10,812

[45] Date of Patent: Mar. 2, 1999

[54] ASTER PLANT NAMED 'ARIEL'

[75] Inventor: Leon Glicenstein, Salinas, Calif.

[73] Assignee: Yoder Brothers, Inc., Barberton, Ohio

[21] Appl. No.: 694,297

[22] Filed: Aug. 8, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 7,399 12/1990 Turtkovic-Sahin ..... Plt./68.1
P.P. 7,400 12/1990 Turtkovic-Sahin ..... Plt./68.1
P.P. 8,384 9/1993 Akerboom ..... Plt./68.1

*Primary Examiner*—Howard J. Locker
*Assistant Examiner*—Kent L. Bell
*Attorney, Agent, or Firm*—Foley & Lardner

[57] ABSTRACT

An Aster plant named 'Ariel' particulary characterized by its cupped capitulum form; daisy capitulum type; lavender-purple ray floret color; diameter across face of capitulum of 32 to 38 mm when fully opened; well branched flower stems; many capitula per inflorescence on short peduncles; flowers hold color well as they age; plant height of 22 to 25 cm when grown in fall under natural daylength with no growth regulators; natural season flower date of August 13 to September 3 when planting rooted cuttings on June 17 to 18 in Salinas, Calif.; and rounded plant habit.

1 Drawing Sheet

The present invention comprises a new and distinct cultivar of Aster plant, botanically known as *Aster hybrida*, and refferred to by the cultivar name 'Ariel'.

'Ariel' is the product of an open-pollinated breeding program, which had the objective of creating new perennial Aster cultivars for pots, garden and landscape use capable of year-round production, as well as having well branched flower stems, a good plant habit, good flower size, and good flower keeping quality. Such traits in combination were not present in previously available commercial varieties.

'Ariel' originated from seed produced on selected parents in an open pollinated field situation in Salinas, Calif. in October 1991. After harvest the seed was bulked, so that the female and the male parents of 'Ariel' are unknown. The seed was sown in Alva, Fla. on Jun. 15, 1992.

'Ariel' was discovered and selected as one flowering plant within the above progeny in February 1993 in a controlled environment in Alva, Fla. by a technician working under the supervision of Leon Glicenstein.

The first act of asexual reproduction of 'Ariel' was accomplished when vegetative cuttings were taken from the initial selection in May of 1993 in a controlled environment in Alva, Fla. by technicians working under the supervision of Leon Glicentstein.

Horticultural examination of controlled flowerings of successive plantings has shown that the unique combination of characteristics as herein disclosed for 'Ariel' are firmly fixed and are retained through successive generations of asexual reproduction.

'Ariel' has been observed under all possible environmental conditions. The phenotype may vary significantly with variations in environment such as temperature, light intensity and daylength, without, however, any variance in genotype.

The following observations, measurements and comparisons describe plants grown in 15 cm pots in controlled open areas in Salinas, Calif. Rooted cuttings were planted in pots and maintained outdoors under the natureal temperature and daylength prevailing during June through October.

The following traits have been repeatedly observed and are determined to be basic characteristics of 'Ariel', which, in combination, distinguished this Aster as a new and distinct cultivar:

1. Cupped capitulum form.

2. Daisy capitulum type.
3. Lavender-purple ray floret color.
4. Diameter across face of capitulum of 32 to 38 mm when fully opened.
5. Well branched flower stems.
6. Many capitula per inflorescence on short peduncles.
7. Flowers hold color well as they age.
8. Plant height of 22 to 25 cm when grown in fall under natural daylength with no growth regulators.
9. Natural season flower date of August 13 to September 3 when planting rooted cuttings on June 17 to 18 in Salinas, Calif.
10. Rounded plant habit.

The accompanying photographic drawing shows a typical plant of 'Ariel', with the colors being as nearly true as possible with illustrations of this type.

Of the commercial cultivars known to the inventor, the most similar in comparison to 'Ariel' is the cultivar identified as 'Blue Butterfly', disclosed in U.S. Plant Pat. No. 7,399. Reference is made to attached Chart A, which compares certain characteristics of Ariel to the same characteristics of 'Blue Butterfly'.

Similar traits are capitulum form and type. Ariel has a more lavender-purple ray floret color (RHS 75B to 76A) than 'Blue Butterfly' (R.H.S. 92B). Ariel has a more rounded, fuller plant habit, a larger diameter of capitulum and a better ray and disc floret color retention than 'Blue Butterfly'.

In the following description color references are made to The Royal Horticultural Society Colour Chart. The color values were determined on plant material grown outdoors in Leamington, Ontario, Canada in September 1995.

Classification:

*Botanical.*—Aster hybrida cv 'Ariel'

*Commercial.*—Perennial garden or landscape Aster.

Inflorescence

A. Capitulum:

*Form.*—Cupped

*Type.*—Daisy.

*Diameter across face.*—32 to 38 mm when fully opened.

B. Corolla of ray florets:
*Color (general tonality from a distance of three meters)* .—Lavender-purple.
*Color (upper surface)*.—Between 75B and 76A.
*Color (under surface)*.—Between 75C and 76C.
*Shape*.—Narrow, oblanceolate to linear, apex obtuse.
*Size*.—13 to 15 mm long, 1 to 2 mm wide.
*Number of ray florets*.—22 to 26.

C. Corolla of discs florets:
*Color (mature)*.—Between 155B and 1D.
*Color (immature)*.—Between 1C and 1D.

D. Reproductive organs:
*Androecium*.—Present on disc florets only; scant pollen.
*Gynoecium*.—Present on both ray and disc florets.

Plant

A. General appearance:
*Height*.—22 to 25 cm when grown in fall under natural daylength with no growth regulators.
*Habit*.—Very well branched, rounded mound.

B. Foliage:
*Color (upper surface)*.—137A.
*Color (under surface)*.—146B
*Shape*.—Oblanceolate to linear, 90 to 100 mm long, 12 to 16 mm wide.
*Margin*.—Entire.
*Arrangement*.—Alternate.

CHART A

COMPARISONS MADE OF PLANTS GROWN UNDER NATURAL SEASON OUTDOOR CONDITIONS IN SALINAS, CALIFORNIA

| CULTIVAR | 'ARIEL' | 'BLUE BUTTERFLY' |
|---|---|---|
| Ray floret color | Lavender-purple | Blue-violet |
| Capitulum form and type | Cupped daisy | Cupped daisy |
| Diameter across face of capitulum | 32 to 38 mm | 27 to 30 mm |
| Plant habit | Rounded mound | Upright mound |
| Nat. season flower date in Salinas, CA | Aug 13 to Sept 3 | Aug 17 to 23 |
| Color retention | Good | Poor |

What is claimed is:

1. A new and distinct Aster plant named 'Ariel', as described and illustrated.

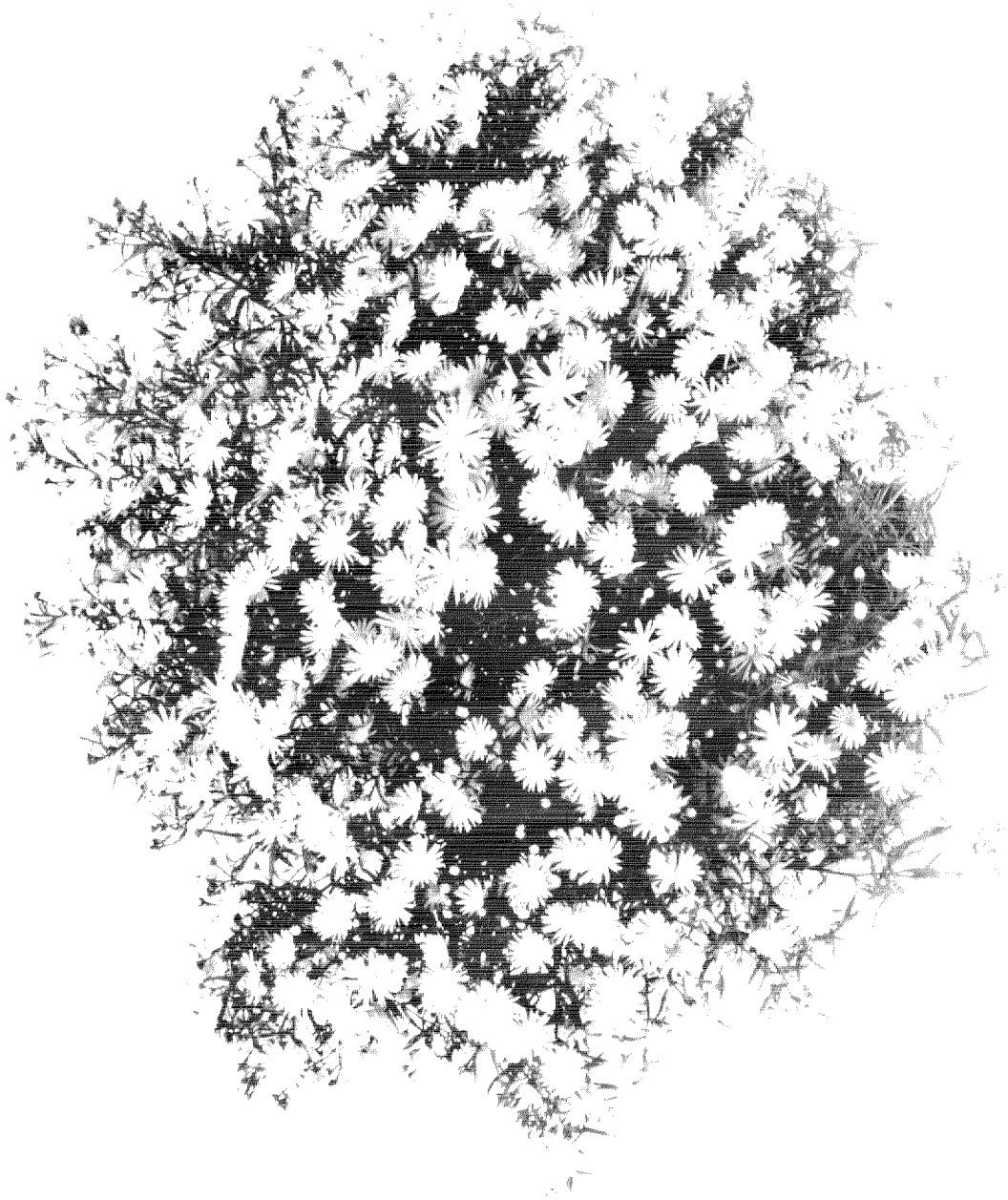

* * * * *